United States Patent [19]
Saxton

[11] Patent Number: 5,824,707
[45] Date of Patent: Oct. 20, 1998

[54] METHOD FOR IMPROVING THE WEIGHT GAIN AND FEED CONVERSION EFFICIENCY OF SWINE

[75] Inventor: Gary B. Saxton, Houston, Tex.

[73] Assignee: Griffin Corporation, Valdosta, Ga.

[21] Appl. No.: 828,954

[22] Filed: Mar. 28, 1997

[51] Int. Cl.⁶ .................................................. A61K 31/30
[52] U.S. Cl. ........................................................... 514/499
[58] Field of Search ............................................... 514/499

[56] References Cited

U.S. PATENT DOCUMENTS

| | | | |
|---|---|---|---|
| 3,231,466 | 1/1966 | Hoffman et al. | 167/53 |
| 3,916,027 | 10/1975 | Taylor | 424/329 |
| 4,326,523 | 4/1982 | Wolfrom et al. | 128/260 |
| 4,956,188 | 9/1990 | Anderson | 426/74 |
| 5,459,162 | 10/1995 | Saxton | 514/499 |

FOREIGN PATENT DOCUMENTS

| | | |
|---|---|---|
| 827521 | 3/1957 | United Kingdom . |
| 1050665 | 7/1964 | United Kingdom . |
| 2083997 | 9/1981 | United Kingdom . |

OTHER PUBLICATIONS

Chemical Abstracts vol.69: 33877u (Dowdy et.al.) 1968.

North, M.O. and Bell, D.D., Commercial Chick Production Manual, Chapman & Hall, p. 599, 4th Ed., 1990.

Kirchgessner et al, The Dynamics of Copper Absorption, 1970.

Schultze et al, Further Studies on the Availability of Copper From Various Sources as a Supplement to Iron in Hemoglobin Formation, J. Biol. Chem., 115:453 (1936).

Gorbet, A.I., Storage of Vitamin A in Broilers on Diets Containing Trace Element Chelates, Nauchnotekhnicheskii Byulleten' Ukrainskogo Nauchno–issledovatel'skogo Instituta Ptitsevodstva, No. 18, pp. 22–24, In Russian, (Ja:8707).

*Primary Examiner*—Leonard Schenkman
*Attorney, Agent, or Firm*—Jones & Askew

[57] ABSTRACT

There is disclosed a method for improving the weight gain of swine. The invention also comprises a method of improving the feed conversion efficiency of swine. The improved method comprises administering orally to swine an effective amount of copper citrate and an amount of feed sufficient to produce weight gain in swine.

9 Claims, No Drawings

METHOD FOR IMPROVING THE WEIGHT GAIN AND FEED CONVERSION EFFICIENCY OF SWINE

FIELD OF THE INVENTION

The present invention relates generally to mineral feed supplements for swine, and, more specifically, to a copper feed supplement for swine. The present invention also relates to a method of increasing the weight gain of swine, such as pigs and hogs, using a copper feed supplement.

BACKGROUND OF THE INVENTION

It is known in the art to treat swine with copper in order to improve their weight gain and to prevent nutritional anemia. The copper requirements of swine is described in M. Edmonds et al., "Feed Additive Studies with Newly Weaned Pigs: Efficacy of Copper, Antibiotics and Citric Acid," 1983, as follows:

Supplementation of swine diets with 250 ppm copper (from $CuSO_4.5H_2O$) markedly and consistently improved rate and efficiency of gain of weanling pigs, particularly during the one-week post weaning stress period.

Generally, copper sulfate is administered to the swine by mixing or dry blending it in with their daily feed, which typically comprises corn and soybean meal. A typical prior art swine feed with blended copper sulfate is prepared by dry blending one to two pounds of copper sulfate with one ton of swine feed. The copper sulfate is therefore administered to the swine at a rate of 125 ppm–250 ppm copper metal equivalent.

Although the copper sulfate produces improved weight gain in swine compared to untreated swine, any further improvement would be of tremendous value to the swine industry. Furthermore, the copper in the copper sulfate is excreted by the swine in their feces. This produces a significant disposal problem for swine farmers.

U.S. Pat. No. 3,231,466 relates to a composition for treating animals, including poultry. This patent discloses that the composition enhances the growth response and/or the general health of domesticated animals. The composition comprises iodine in an organic form, either choline iodine or ethylene dihydroiodide; phthalylsulfacetamide; and iron, cobalt and copper in the form of choline citrate complexes. The patent further discloses that:

Iron is not fully utilized, however, without available copper and cobalt. For these reasons copper sulfate and cobalt sulfate became parts of the original composition. It has subsequently been determined through continuing research that the choline citrate compounds of copper and cobalt are far more desirable in that they are less toxic, more readily available, and therefore, serve more adequately to enhance absorption and utilization of the iron than do the inorganic compounds, thereby greatly stimulating hemoglobin rise and increased red blood cell counts.

Although this patent discloses copper choline citrate, it is apparent that the focus of the invention was on the addition of choline to the composition; not the addition of copper in a citrate form.

Choline is know to be an aid to the growth of chickens. As disclosed by M. O. North and D. D. Bell, "Commercial Chick Production Manual," Chapman & Hall, p. 599, 4th Ed., 1990:

The chick's demand for choline is great. Choline forms a part of the phospholipid, lecithin, rather than an enzyme. Therefore, choline is seldom considered a true vitamin. At times it may be synthesized by the chick, but the amounts are small and usually inadequate. The older a bird gets, the better the synthesis.

The vitamin has a great many functions in the body: It helps in fat movement in the bloodstream; it has a sparing action on methionine; it aids in growth; it prevents a type of slipped tendon; and it helps to reduce excessive fat deposits in the liver.

In view of this prior art, one would expect that the removal of the choline from the copper choline citrate complex would not produce an improvement in the growth of poultry.

In Kirchgessner et al., "The Dynamics of Copper Absorption," 1970, it is stated that:

Improved Cu absorption [intestinal wall absorption] was found in Cu complexes with organic acids also. Specific effects, however, have still not been observed . . . .

In Schultze et al, "Further Studies on the Availability of Copper m Various Sources Supplement to Iron in Hemoglobin Formation," J. Biol. Chem. 115:453 (1936), various copper sources were examined for copper availability to supplement iron in hemoglobin formation. The copper in copper citrate, copper sulfate and other copper sources were all found to be readily available.

U.S. Pat. No. 5,459,162 relates to a method of improving weight gain in chickens and to a method of improving feed conversion efficiency in chickens. The method comprises administering orally to chickens between approximately 50 and 125 ppm copper metal equivalent from copper citrate and an amount of chicken feed sufficient to produce weight gain in chickens. However, this patent provides no suggestion that copper citrate would be effective in treating swine.

The foregoing references indicate that copper citrate is equivalent in terms of bioavailability to copper sulfate and that copper citrate produces improved weight gain and feed conversion in chickens.

Therefore, a need exists for a feed supplement which produces less toxic waste while maintaining or improving the weight gain of swine treated therewith. Furthermore, there is also a need for a form of copper which enhances the growth response of swine, but which does not include choline as a complex with copper.

SUMMARY OF THE INVENTION

The present invention satisfies the above-described needs by providing an improved method of increasing the growth response and/or weight gain in swine and a method of improving the feed conversion efficiency of swine. The improved method of the present invention comprises the step of administering orally to swine an effective amount of copper citrate.

Accordingly, it is an object of the present invention to provide an improved method for enhancing weight gain in swine.

Another object of the present invention is to provide a method which enhances weight gain in swine at lower levels of copper.

A further object of the present invention is to provide a method of enhancing weight gain in swine which is less polluting to the environment.

Yet another object of the present invention is to provide a method of treating swine which causes the swine to more efficiently convert their feed to body weight.

These and other objects, features and advantages of the present invention will become apparent after a review of the following detailed description of the disclosed embodiments and the appended claims.

DETAILED DESCRIPTION OF THE DISCLOSED EMBODIMENTS

The present invention relates to an improved method for producing weight gain in swine, such as pig and hogs. The present invention also relates to a method of improving the feed conversion efficiency of swine. The novel method of the present invention comprises the steps of administering orally to swine an amount of copper citrate effective to improve the weight gain of swine or to improve the efficiency of feed conversion. An amount of feed sufficient to produce weight gain is also administered to the swine.

Copper citrate has the chemical formula $C_6H_4Cu_2O_7$. Copper citrate is prepared by reacting either copper carbonate —$Cu_2(OH)_2CO_3$— or copper hydroxide —$Cu(OH)_2$— with citric acid —$C_6H_8O_7$. Copper citrate can also be prepared by reacting sodium citrate (trisodium citrate) —$C_6H_5O_7Na_3 \cdot 2H_2O$— with copper sulfate —$CuSO_4$. The resulting reaction produces copper citrate in an aqueous medium. The copper citrate, which is a solid, will precipitate from the aqueous phase and can be separated by simple filtration and drying. Copper citrate is also available from several commercial sources, such as Weinstein Chemicals, Inc. of Costa Mesa, Calif.

In accordance with the present invention, it has been discovered that copper citrate will produce the same, or greater, weight gain in swine as copper sulfate, but at approximately one-half the dose of copper metal equivalent as copper sulfate. In the prior art, copper sulfate has typically been administered to swine at a rate of 125 ppm to 250 ppm copper metal equivalent. However, in accordance with the present invention, it has been discovered that the same, or better, results can be accomplished by treating swine with copper citrate at a rate of approximately 50 ppm to 125 ppm copper metal equivalent; preferably, 63 ppm copper metal equivalent.

The particular swine feeds which are useful in the present invention are not critical. Generally, those feeds which have been used in the prior art to feed swine, particularly pigs and hogs, are suitable for use in the present invention. Typical swine feeds which are useful in the present invention may contain mixtures of the following: carbohydrates, such as, barley; buckwheat; cassava; corn, for example, yellow corn, white corn and high-lysine corn; millet (proso); molasses; oats; rice; rye; sorghums, for example, kafir and milo; triticale; and wheat; mill by-products, such as, hominy feed; rice bran; rice hulls; wheat by-products, for example, wheat bran and wheat millings, shorts; fats and oils, such as, hard fats from slaughtered cattle; soft fats, for example, yellow grease; hydrolyzed animal fats; vegetable oils; and polyunsaturated fatty acids in egg yolks; proteins of animal origin, such as, dried blood; dried poultry waste, for example, dried cage layer manure; liver meal; meat by-products, for example, meat scraps and meat and bone meal; milk products, such as, dried skim milk; dried butter milk, and dried whey; poultry by-products, such as, hydrolyzed poultry feather meal; poultry hatchery by-product meal, for example, eggshells, unhatched and infertile eggs, and culled chicks; proteins of fish origin, such as, white fish meal; dark fish meal; and shrimp meal; proteins of vegetable origin, such as, corn gluten, coconut (copra) oil meal; cottonseed meal; guar meal; linseed (flax) oil meal; peanut (groundnut) meal; rapeseed oil meal (canola meal); safflower meal; sesame meal; soybean meal; full-fat soybeans; and sunflower seed meal; green leafy products, such as, alfalfa products, for example, sun-cured alfalfa meal, dehydrated alfalfa meal, and dehydrated alfalfa leaf meal; macrominerals, such as, curaçau (island) rock phosphate ($CaHPO_4$) ($CaHPO_4 \cdot H_2O$); dicalcium phosphate ($CaHPO_4 \cdot 2H_2O$); rock phosphate; steamed bone meal ($Ca_3(PO_4)_2$); argonite ($CaCO_3$); limestone ($CaCO_3$); oyster shell ($CaCO_3$); gypsum ($CaSO_4 \cdot 2H_2O$) and salt (NaCl); and vitamins, minerals and trace ingredient, such as, fat-soluble vitamins, for example, vitamins A, D, E, and K; water-soluble vitamins, for example, C (ascorbic acid), thiamin ($B_1$), riboflavin ($B_2$), pantothenic acid, niacin, pyridoxine ($B_6$), choline, biotin, folacin (folic acid), $B_{12}$ (cobalamin); minerals, such as, calcium; phosphorus; vitamin D; sodium; chlorine; potassium; sulfur; iodine; fluorine; iron; copper; manganese; magnesium; selenium; vanadium; and zinc; amino acids, such as, methionine; cystine; lysine; tryptophan; and arginine; and other feed constituents, such as, antibiotics; arsenicals; xanthophylls; antioxidants; coccidiostat; electrolytes; pellet binders; tranquilizers and other supplements, for example, flavoring agents, enzymes, thyroactive compounds, and drugs.

A copper citrate formulation in accordance with the present invention may be produced in accordance with the present invention by the following steps. Swine feed, such as a pig feed, comprising ground corn and soy bean meal, is dry blended with copper citrate in powder form so that the copper citrate is uniformly distributed throughout the pig feed. Apparatus for dry blending such components is well known to those skilled in the art. The swine feed containing the blended copper citrate is then fed to swine, such as pigs, so that the copper citrate is consumed by the pigs orally along with the pig feed. Although the foregoing discloses mixing the copper citrate with swine feed, it is also specifically contemplated that the copper citrate and the swine feed can be administered to the swine separately.

There is no particular upper limit for the concentration of the copper citrate which can be administered to the swine. However, large doses of copper citrate may be toxic to swine and should therefore be avoided. Furthermore, greater amounts of copper citrate do not produce directly proportional weight gains. The copper citrate can be added to the swine feed in amounts sufficient to enhance the weight gain and/or feed conversion efficiency of the swine. Optimum concentrations of the copper citrate useful in the present invention are between approximately 50 ppm and 125 ppm copper metal equivalent; preferably approximately 63 ppm copper metal equivalent. These dosage rates can be achieved by dry blending between approximately 0.25 lbs and 0.62 lbs of copper citrate, preferably approximately 0.31 lbs of copper citrate, with one ton of swine feed.

The copper citrate is administered to the swine after the swine are weaned. Weaning generally takes place at an age of four weeks. Although copper citrate can be administered to swine throughout their growth period, it is preferred that the copper citrate be administered to the swine during the first seven-day post-weaning period, most preferably during the first fourteen-day post-weaning period. During this two-week post-weaning period, the swine will receive the maximum benefit of the copper citrate treatment.

The following examples are illustrative of the present invention and are not intended to limit the scope of the invention as set forth in the appended claims. All temperatures are in degrees Celsius and all percentages are by weight unless specifically stated otherwise.

EXAMPLE 1

A total of 270 pigs weaned at 25 days (+/−3 days) having an average initial weight of 7.4 kg were allotted by weight, sex and ancestry to one of six experimental treatments in a randomized complete block. Diets were corn/soybean meal-based as shown in Table 1 below:

TABLE 1

| Ingredient | Percentage as fed |
|---|---|
| corn | 48.60 |
| soybean meal, 48% | 23.72 |
| whey | 15.00 |
| fish meal | 5.00 |
| animal fat | 5.00 |
| dicalcium phosphate | 1.14 |
| limestone | 0.61 |
| L-lysine | 0.18 |
| salt | 0.25 |
| trace minerals[a] | 0.25 |
| vitamins[b] | 0.25 |

[a]Provided per kilogram of diet: 15 mg Cu ($CuSO_4.5H_2O$); 150 mg Fe; 200 mg Zn; 10 mg Mn; 0.15 mg I; and 0.30 mg Se.
[b]Provided per kilogram of diet: 4,400 IU vitamin A; 440 IU vitamin $D_3$; 22 IU vitamin E; 1.1 mg vitamin K; 4.4 mg riboflavin; 22 mg d-pantothenic acid; 22 mg vitamin $B_{12}$; 0.61 g choline (choline chloride); 0.14 mg d-biotin; and 0.66 mg folic acid.

The control diet contained 15 ppm Cu from copper sulfate. Experimental diets included the addition of 0, 125 or 250 ppm Cu from copper sulfate or 32, 63 or 125 ppm Cu from copper citrate. The copper compounds were substituted for equal weights of corn in all diets.

Pigs were weighed at weaning and then weekly throughout the 28 day trial. Feed disappearance or consumption was measured weekly. Feed efficiency was calculated as the amount of weight gain divided by the amount of feed consumed. The pen was considered the experimental unit. Data was analyzed using the General Linear Model SAS. The results of the test are shown in Tables 2–4 below.

TABLE 2

GROWTH PERFORMANCE-
AVERAGE DAILY WEIGHT GAIN (GRAMS/DAY)

| | | Copper Sulfate (ppm) | | Copper Citrate (ppm) | | | |
|---|---|---|---|---|---|---|---|
| Period | 15 Control | 125 | 250 | 32 | 63 | 125 | SE |
| day 1–14 | 63[a] | 140[b] | 121[bc] | 92[ac] | 116[bc] | 117[bc] | 13 |
| day 14–28 | 508[c] | 563[b] | 604[bc] | 566[b] | 585[ac] | 623[c] | 19 |
| day 1–28 | 285[a] | 351[bc] | 362[bc] | 329[b] | 351[bc] | 370[c] | 13 |

TABLE 3

FEED CONSUMPTION-
AVERAGE DAILY FEED INTAKE (GRAMS/DAY)

| | | Copper Sulfate (ppm) | | Copper Citrate (ppm) | | | |
|---|---|---|---|---|---|---|---|
| Period | 15 Control | 125 | 250 | 32 | 63 | 125 | SE |
| day 1–14 | 231[1] | 326[b] | 288[c] | 269[c] | 269[c] | 279[c] | 13 |
| day 14–28 | 804[a] | 972[b] | 1007[b] | 927[c] | 931[b] | 988[b] | 35 |
| day 1–28 | 517[a] | 649[b] | 648[b] | 593[b] | 600[b] | 633[b] | 22 |

TABLE 4

FEED CONVERSION-
GAIN/FEED (GRAMS/GRAM)

| | | Copper Sulfate (ppm) | | Copper Citrate (ppm) | | | |
|---|---|---|---|---|---|---|---|
| Sample | Control | 125 | 250 | 32 | 63 | 125 | SE |
| day 1–14 | 0.277[c] | 0.420[bc] | 0.424[bc] | 0.339[ac] | 0.423[bc] | 0.418[bc] | 0.039 |
| day 14–28 | 0.633[c] | 0.582[bc] | 0.602[ac] | 0.615[ac] | 0.632[a] | 0 631[a] | 0.013 |
| day 1–28 | 0.552[ab] | 0.542[b] | 0.562[ab] | 0.551[ab] | 0.586[a] | 0.585[a] | 0.013 |

[abc]Means with different superscripts differ P < 0.05.

As can be seen from Table 2, for the period day 1–28, the pigs that were treated with copper citrate (125 ppm) gained 19 grams per day more than the swine treated with the copper sulfate (125 ppm), 8 grams per day more than the swine treated with the copper sulfate (250 ppm) and 85 grams per day more than the untreated swine (control). For the period day 14–28, the pigs that were treated with copper citrate (125 ppm) gained 60 grams per day more than the swine treated with the copper sulfate (125 ppm), 19 grams per day more than the swine treated with the copper sulfate (250 ppm) and 115 grams per day more than the untreated swine (control).

As can be seen from Table 3, for the period day 1–28, the pigs that were treated with copper citrate (125 ppm) consumed 16 grams per day less feed than the swine treated with the copper sulfate (125 ppm), 15 per day grams less feed than the swine treated with the copper sulfate (250 ppm) and 66 grams per day more feed than the untreated swine (control). For the period day 14–28, the pigs that were treated with copper citrate (125 ppm) consumed 16 grams per day less feed than the swine treated with the copper sulfate (125 ppm), 15 grams per day less feed than the swine treated with the copper sulfate (250 ppm) and 116 grams per day more feed than the untreated swine (control).

As can be seen from Table 4, for the period day 1–28, the pigs that were treated with copper citrate (125 ppm) converted their feed more efficiently (0.585 grams of weight gain per gram of feed intake) than the swine treated with the copper sulfate (125 ppm) (0.542 g/g), more efficiently (0.585 g/g) than the swine treated with the copper sulfate (250 ppm) (0.562 g/g) and more efficiently (0.585 g/g) than the untreated swine (control) (0.552 g/g). For the period day 14–28, the pigs that were treated with copper citrate (125 ppm) converted their feed more efficiently (0.631 g/g) than the swine treated with the copper sulfate (125 ppm) (0.582 g/g), more efficiently (0.631 g/g) than the swine treated with the copper sulfate (250 ppm) (0.602 g/g) and less efficiently (0.631 g/g) than the untreated swine (control) (0.633 g/g). For the period day 1–28, the pigs that were treated with copper citrate (63 ppm) converted their feed more efficiently (0.586 g/g) than the swine treated with the copper sulfate (125 ppm) (0.542 g/g), more efficiently (0.586 g/g) than the swine treated with the copper sulfate (250 ppm) (0.562 g/g) and more efficiently (0.586 gig) than the untreated swine (control) (0.552 g/g). For the period day 14–28, the pigs that were treated with copper citrate (63 ppm) converted their feed more efficiently (0.632 g/g) than the swine treated with the copper sulfate (125 ppm) (0.582 g/g), more efficiently (0.631 g/g) than the swine treated with the copper sulfate (250 ppm) (0.602 g/g) and less efficiently (0.632 g/g) than the untreated swine (control) (0.633 g/g).

EXAMPLE 2

The same procedure as Example 1 was followed, except that one hundred pigs allotted to one of four experimental treatments in a randomized complete block. Diets used in this example were identical to those identified in Example 1. Experimental treatments were 0 or 250 ppm Cu from copper sulfate or 50 or 100 ppm Cu from copper citrate. The results of this test are shown in Tables 5–7 below.

TABLE 5

GROWTH PERFORMANCE-
AVERAGE DAILY WEIGHT GAIN (GRAMS/DAY)

| | Copper Sulfate (ppm) | | Copper Citrate (ppm) | | | |
|---|---|---|---|---|---|---|
| Period | 0 | 250 | 50 | 100 | SE | P Value |
| day 1–14 | 110$^a$ | 193$^b$ | 146$^c$ | 173$^c$ | 13 | 0.01 |
| day 14–28 | 434$^a$ | 523$^b$ | 522$^b$ | 500$^b$ | 28 | NS |
| day 1–28 | 272$^a$ | 358$^b$ | 334$^b$ | 336$^b$ | 17 | 0.05 |

TABLE 6

FEED CONSUMPTION-
AVERAGE DAILY FEED INTAKE (GRAMS/DAY)

| | Copper Sulfate (ppm) | | Copper Citrate (ppm) | | | |
|---|---|---|---|---|---|---|
| Sample | 0 | 250 | 50 | 100 | SE | P Value |
| day 1–14 | 261$^a$ | 373$^b$ | 328$^a$ | 310$^a$ | 19 | 0.01 |
| day 14–28 | 668$^a$ | 854$^b$ | 832$^b$ | 802$^b$ | 42 | 0.05 |
| day 1–28 | 464$^a$ | 613$^b$ | 580$^{bc}$ | 556$^a$ | 25 | 0.01 |

TABLE 7

FEED CONVERSION-
GAIN/FEED (GRAMS/KILOGRAM)

| | Copper Sulfate (ppm) | | Copper Citrate (ppm) | | | |
|---|---|---|---|---|---|---|
| Sample | 0 | 250 | 50 | 100 | SE | P Value |
| day 1–14 | 417$^a$ | 518$^a$ | 441$^a$ | 555$^b$ | 27 | 0.05 |
| day 14–28 | 654$^a$ | 617$^{bc}$ | 632$^{ac}$ | 624$^c$ | 14 | NS |
| day 1–28 | 587$^a$ | 588$^a$ | 579$^a$ | 605$^a$ | 15 | NS |

$^{abc}$Means with different superscripts differ P < 0.05.

As can be seen from Table 5, for the period day 1–28, the pigs that were treated with copper citrate (100 ppm) gained 22 grams per day less than the swine treated with the copper sulfate (250 ppm) and 64 grams per day more than the untreated swine (control). For the period day 14–28, the pigs that were treated with copper citrate (100 ppm) gained 23 grams per day less than the swine treated with the copper sulfate (250 ppm) and 66 grams per day more than the untreated swine (control).

As can be seen from Table 6, for the period day 1–28, the pigs that were treated with copper citrate (100 ppm) consumed 57 grams per day less feed than the swine treated with the copper sulfate (250 ppm) and 92 grams per day more feed than the untreated swine (control). For the period day 14–28, the pigs that were treated with copper citrate (50 ppm) consumed 33 grams per day less feed than the swine treated with the copper sulfate (250 ppm) and 116 grams per day more feed than the untreated swine (control).

As can be seen from Table 7, for the period day 1–28, the pigs that were treated with copper citrate (100 ppm) converted their feed more efficiently (605 grams of weight gain per kg of feed intake) than the swine treated with the copper sulfate (250 ppm) (588 g/kg) and more efficiently (605 g/kg) than the untreated swine (control) (587 g/kg). For the period day 14–28, the pigs that were treated with copper citrate (100 ppm) converted their feed more efficiently (624 g/kg) than the swine treated with the copper sulfate (250 ppm) (617 g/kg) and less efficiently (624 g/kg) than the untreated swine (control) (654 g/kg). For the period day 1–28, the pigs that were treated with copper citrate (50 ppm) converted their feed approximately equally efficiently (579 g/kg) as the swine treated with the copper sulfate (250 ppm) (588 g/kg) and approximately equally efficiently (579 g/kg) as the untreated swine (control) (587 g/kg). For the period day 14–28, the pigs that were treated with copper citrate (50 ppm) converted their feed more efficiently (632 g/kg) than the swine treated with the copper sulfate (250 ppm) (617 g/kg) and less efficiently (632 g/kg) than the untreated swine (control) (654 g/kg).

EXAMPLE 3

The same procedure as Example 1 was followed, except that 110 pigs were allotted to one of five experimental treatments in a randomized complete block. The five experimental treatments used in this example are identified in Tables 8 and 9 below. The five experimental treatments were 0 ppm Cu (control), 62.5 or 125 ppm Cu from copper citrate and 125 or 250 ppm Cu from copper sulfate.

TABLE 8

TREATMENTS (Percentage by Weight)

| | Treatment No. | | | | |
|---|---|---|---|---|---|
| Ingredient | 1 | 2 | 3 | 4 | 5 |
| Corn | 48.75 | 48.73 | 48.71 | 48.72 | 48.70 |
| SBM-48 | 28.75 | 28.75 | 28.75 | 28.75 | 28.75 |
| Whey, dried | 20.00 | 20.00 | 20.00 | 20.00 | 20.00 |
| Dical phos | 1.28 | 1.28 | 1.28 | 1.28 | 1.28 |
| Limestone | 0.60 | 0.60 | 0.60 | 0.60 | 0.60 |
| Salt, iod. | 0.35 | 0.35 | 0.35 | 0.35 | 0.35 |
| Vitamin mix | 0.10 | 0.10 | 0.10 | 0.10 | 0.10 |
| T-mineral mix | 0.08 | 0.08 | 0.08 | 0.08 | 0.08 |
| Aureo-50 | 0.10 | 0.10 | 0.10 | 0.10 | 0.10 |
| Copper citrate | — | 0.0163 | 0.0326 | — | — |
| Copper sulfate | — | — | — | 0.0250 | 0.0500 |

TABLE 9

TREATMENTS (Weights in Pounds)

| | Treatment No. | | | | |
|---|---|---|---|---|---|
| Ingredient | 1 | 2 | 3 | 4 | 5 |
| Corn | 48.75 | 48.73 | 48.71 | 48.72 | 48.70 |
| SBM-48 | 28.75 | 28.75 | 28.75 | 28.75 | 28.75 |
| Whey, dried | 20.00 | 20.00 | 20.00 | 20.00 | 20.00 |
| Dical phos | 1.28 | 1.28 | 1.28 | 1.28 | 1.28 |
| Limestone | 0.60 | 0.60 | 0.60 | 0.60 | 0.60 |
| Salt, iod. | 0.35 | 0.35 | 0.35 | 0.35 | 0.35 |
| Vitamin mix | 0.10 | 0.10 | 0.10 | 0.10 | 0.10 |
| T-mineral mix | 0.08 | 0.08 | 0.08 | 0.08 | 0.08 |
| Aureo-50 | 0.10 | 0.10 | 0.10 | 0.10 | 0.10 |
| Copper citrate | — | 0.0163 | 0.0326 | — | — |
| Copper sulfate | — | — | — | 0.0250 | 0.0500 |

The results of the test after 7 days is shown in Tables 10–12 below.

TABLE 10

GROWTH PERFORMANCE (7 DAYS)- AVERAGE DAILY WEIGHT GAIN (POUNDS/DAY)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | −0.174 | −0.033 | −0.076 | 0.113 | 0.095 | −0.015 |
| 2 | 0.270 | 0.304 | 0.273 | 0.429 | 0.326 | 0.320 |
| 3 | 0.098 | −0.146 | 0.180 | 0.130 | 0.018 | 0.056 |
| 4 | 0.090 | 0.093 | 0.188 | 0.116 | −0.011 | 0.095 |
| Average | 0.071 | 0.054 | 0.141 | 0.197 | 0.107 | |

TABLE 11

FEED CONSUMPTION (7 DAYS)- AVERAGE DAILY FEED INTAKE (POUNDS/DAY)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 0.143 | 0.343 | 0.400 | 0.400 | 0.309 | 0.319 |
| 2 | 0.583 | 0.583 | 0.571 | 0.804 | 0.696 | 0.648 |
| 3 | 0.406 | 0.299 | 0.486 | 0.321 | 0.451 | 0.378 |
| 4 | 0.280 | 0.438 | 0.321 | 0.237 | 0.208 | 0.297 |
| Average | 0.353 | 0.398 | 0.445 | 0.440 | 0.416 | |

TABLE 12

FEED CONVERSION (7 DAYS)- FEED/GAIN (POUNDS/POUND)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | −0.820 | −10.435 | −5.283 | 3.544 | 3.265 | −1.946 |
| 2 | 2.159 | 1.922 | 2.096 | 1.875 | 2.135 | 2.037 |
| 3 | 4.135 | −1.569 | 2.698 | 2.473 | 25.240 | 6.595 |
| 4 | 3.092 | 4.712 | 1.714 | 2.045 | −19.444 | −1.576 |
| Average | 2.141 | −1.343 | 0.306 | 2.484 | 2.799 | |

The results of the test after 14 days is shown in Tables 13–15 below.

TABLE 13

GROWTH PERFORMANCE (14 DAYS)- AVERAGE DAILY WEIGHT GAIN (POUNDS/DAY)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 0.238 | 0.319 | 0.319 | 0.428 | 0.471 | 0.369 |
| 2 | 0.605 | 0.527 | 0.520 | 0.679 | 0.627 | 0.592 |
| 3 | 0.250 | 0.288 | 0.429 | 0.504 | 0.455 | 0.385 |
| 4 | 0.260 | 0.301 | 0.460 | 0.340 | 0.215 | 0.315 |
| Average | 0.338 | 0.359 | 0.450 | 0.488 | 0.442 | |

TABLE 14

FEED CONSUMPTION (14 DAYS)- AVERAGE DAILY FEED INTAKE (POUNDS/DAY)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 0.454 | 0.675 | 0.800 | 0.793 | 0.765 | 0.697 |
| 2 | 0.976 | 0.857 | 1.024 | 1.098 | 1.107 | 1.013 |
| 3 | 0.685 | 0.568 | 0.996 | 0.875 | 1.047 | 0.834 |
| 4 | 0.565 | 0.649 | 0.737 | 0.583 | 0.574 | 0.622 |
| Average | 0.670 | 0.687 | 0.889 | 0.837 | 0.837 | |

TABLE 15

FEED CONVERSION (14 DAYS)- FEED/GAIN (POUNDS/POUND)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 1.907 | 2.114 | 2.048 | 1.853 | 1.623 | 1.909 |
| 2 | 1.613 | 1.627 | 1.968 | 1.618 | 1.765 | 1.718 |
| 3 | 2.741 | 1.973 | 2.321 | 1.735 | 2.299 | 2.214 |
| 4 | 2.179 | 2.158 | 1.602 | 1.715 | 2.673 | 2.065 |
| Average | 2.110 | 1.968 | 1.985 | 1.730 | 2.090 | |

The results of the test after 21 days is shown in Tables 16–18 below.

TABLE 16

GROWTH PERFORMANCE (21 DAYS)- AVERAGE DAILY WEIGHT GAIN (POUNDS/DAY)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 0.454 | 0.520 | 0.637 | 0.623 | 0.636 | 0.574 |
| 2 | 0.608 | 0.659 | 0.617 | 0.756 | 0.670 | 0.662 |
| 3 | 0.411 | 0.475 | 0.700 | 0.584 | 0.667 | 0.567 |
| 4 | 0.477 | 0.543 | 0.655 | 0.436 | 0.405 | 0.503 |
| Average | 0.487 | 0.549 | 0.652 | 0.600 | 0.594 | |

TABLE 17

FEED CONSUMPTION (21 DAYS)- AVERAGE DAILY FEED INTAKE (POUNDS/DAY)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 0.769 | 0.950 | 1.200 | 1.138 | 1.226 | 1.057 |
| 2 | 1.254 | 1.171 | 1.327 | 1.427 | 1.484 | 1.333 |
| 3 | 0.927 | 0.914 | 1.426 | 1.117 | 1.579 | 1.193 |
| 4 | 0.887 | 0.912 | 1.092 | 0.779 | 0.869 | 0.908 |
| Average | 0.959 | 0.987 | 1.261 | 1.115 | 1.290 | |

TABLE 18

FEED CONVERSION (21 DAYS)- FEED/GAIN (POUNDS/POUND)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 1.695 | 1.827 | 1.885 | 1.826 | 1.929 | 1.832 |
| 2 | 2.063 | 1.777 | 2.153 | 1.887 | 2.214 | 2.019 |
| 3 | 2.257 | 1.924 | 2.036 | 1.913 | 2.368 | 2.100 |
| 4 | 1.861 | 1.680 | 1.668 | 1.786 | 2.145 | 1.828 |
| Average | 1.969 | 1.802 | 1.935 | 1.853 | 2.164 | |

The results of the test after 28 days is shown in Tables 19–21 below.

TABLE 19

GROWTH PERFORMANCE (28 DAYS)- AVERAGE DAILY WEIGHT GAIN (POUNDS/DAY)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 0.724 | 0.733 | .836 | 0.868 | 0.876 | 0.810 |
| 2 | 0.691 | 0.762 | 0.701 | 0.897 | 0.821 | 0.774 |
| 3 | 0.567 | 0.631 | 0.800 | 0.724 | 0.795 | 0.703 |
| 4 | 0.591 | 0.717 | 0.757 | 0.583 | 0.607 | 0.651 |
| Average | 0.643 | 0.711 | 0.774 | 0.770 | 0.775 | |

TABLE 20

FEED CONSUMPTION (28 DAYS)- AVERAGE DAILY FEED INTAKE (POUNDS/DAY)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 1.145 | 1.354 | 1.568 | 1.495 | 1.569 | 1.426 |
| 2 | 1.445 | 1.374 | 1.565 | 1.695 | 1.738 | 1.563 |
| 3 | 1.155 | 1.177 | 1.646 | 1.391 | 1.889 | 1.452 |
| 4 | 1.192 | 1.242 | 1.489 | 1.027 | 1.177 | 1.225 |
| Average | 1.234 | 1.287 | 1.567 | 1.402 | 1.593 | |

TABLE 21

FEED CONVERSION (28 DAYS)- FEED/GAIN (POUNDS/POUND)

| Repetition | 1 Control | Copper citrate 2 62.5 ppm | Copper citrate 3 125 ppm | Copper sulfate 4 125 ppm | Copper sulfate 5 250 ppm | Average |
|---|---|---|---|---|---|---|
| 1 | 1.580 | 1.847 | 1.847 | 1.702 | 1.709 | 1.759 |
| 2 | 2.091 | 1.803 | 2.234 | 1.889 | 2.117 | 2.027 |
| 3 | 2.037 | 1.864 | 2.57 | 1.923 | 2.378 | 2.052 |
| 4 | 2.017 | 1.731 | 1.968 | 1.764 | 1.938 | 1.883 |
| Average | 1.931 | 1.811 | 2.033 | 1.819 | 2.056 | |

The pigs that received the experimental treatment containing 62.5 ppm copper from copper citrate achieved better feed conversion efficiency than the pigs treated with 125 ppm copper from both sources, i.e., copper citrate and copper sulfate, in the 7, 21 and 28 day time periods.

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A method of improving weight gain or feed conversion efficiency in swine comprising the step of:

administering orally to said swine a composition consisting essentially of an effective amount of copper citrate and an amount of feed sufficient to produce weight gain in said swine.

2. The method of claim 1, wherein said copper citrate is administered to said swine by combining said copper citrate with feed for said swine.

3. The method of claim 2, wherein said copper citrate in said feed is present in an amount between approximately 50 ppm and 125 ppm copper metal equivalent.

4. The method of claim 2, wherein said copper citrate in said feed is present in an amount of approximately 63 ppm copper metal equivalent.

5. The method of claim 1, wherein said swine are selected from the group of pigs and hogs.

6. The method of claim 1, wherein said swine are pigs.

7. The method of claim 1, wherein said swine are hogs.

8. A method of improving weight gain or feed conversion efficiency in swine comprising the step of:

administering orally to said swine during the fourteen-day period post-weaning a composition consisting essentially of an effective amount of copper citrate and an amount of feed sufficient to produce weight gain in said swine.

9. A method of improving weight gain or feed conversion efficiency in swine comprising the step of:

administering orally to said swine during the seven-day period post-weaning a composition consisting essentially of an effective amount of copper citrate and an amount of feed sufficient to produce weight gain in said swine.

* * * * *